(12) United States Patent
Vermeulen et al.

(10) Patent No.: US 9,675,535 B2
(45) Date of Patent: Jun. 13, 2017

(54) TRICLOSAN-FREE ANTIBACTERIAL SOAP

(71) Applicant: RUBBERMAID COMMERCIAL PRODUCTS/US, Winchester, VA (US)

(72) Inventors: Yvan Vermeulen, Wijk Aan Zee (NL); Nirali Patel, Winchester, VA (US); John Van Cassel, Leiden (NL)

(73) Assignee: RUBBERMAID COMMERCIAL PRODUCTS/US, Winchester, VA (US)

( * ) Notice: Subject to any disclaimer, the term of this patent is extended or adjusted under 35 U.S.C. 154(b) by 83 days.

(21) Appl. No.: 14/492,605

(22) Filed: Sep. 22, 2014

(65) Prior Publication Data

US 2016/0081897 A1    Mar. 24, 2016

(51) Int. Cl.
| | |
|---|---|
| *A61K 31/195* | (2006.01) |
| *A61K 8/41* | (2006.01) |
| *A61K 8/365* | (2006.01) |
| *A61K 8/34* | (2006.01) |
| *A61Q 17/00* | (2006.01) |

(52) U.S. Cl.
CPC ............... *A61K 8/41* (2013.01); *A61K 8/34* (2013.01); *A61K 8/365* (2013.01); *A61Q 17/005* (2013.01); *A61K 2800/30* (2013.01)

(58) Field of Classification Search
CPC .................................................. A61K 31/195
USPC ........................................................ 514/561
See application file for complete search history.

(56) References Cited

U.S. PATENT DOCUMENTS

| | | | |
|---|---|---|---|
| 4,938,953 A | 7/1990 | Pena et al. | |
| 6,432,395 B1 | 8/2002 | Rochon et al. | |
| 6,617,294 B2 | 9/2003 | Narula et al. | |
| 7,589,051 B2 | 9/2009 | Erazo-Majewicz et al. | |
| 9,226,882 B2 * | 1/2016 | Konate | A61Q 19/00 |
| 2004/0131569 A1 | 7/2004 | Schneider et al. | |
| 2009/0226541 A1 | 9/2009 | Scholz et al. | |
| 2010/0234328 A1 | 9/2010 | Ahmed et al. | |
| 2013/0172415 A1 | 7/2013 | Vermeulen et al. | |

FOREIGN PATENT DOCUMENTS

| | | |
|---|---|---|
| CA | 2130284 A1 | 3/1995 |
| EP | 0588912 A1 | 3/1994 |
| EP | 0640285 A1 | 3/1995 |
| KR | 102008001803 | 2/2008 |
| WO | WO-2008/061375 A1 | 5/2008 |
| WO | WO-2008/157847 A1 | 12/2008 |

OTHER PUBLICATIONS

Dissolvine® GL Technical brochure, AkzoNobel Functional Chemicals Chelates, available before Sep. 22, 2014.
Ehow, "What is sodium lauryl sulfate?", retrieved on Dec. 19, 2014 from the Internet at: <http://www.ehow.com/6320871_sodium-laureth-sulfate_.html>.
European Standard (EN1499), Chemical Disinfectants and Antiseptics—Hygienic Handwash—Test Method and Requirements (phase 2/step 2) (Mar. 1997).
Federal Register, vol. 59, No. 116, p. 31412 (Jun. 17, 1994).
Federal Register, vol. 59, No. 116, pp. 31402-31452 (Jun. 17, 1994).
International Search Report and Written Opinion for international application No. PCT/US2012/071826, mailing date Jul. 29, 2013.
Methylisothiazolinone, retrieved on Dec. 19, 2014 from the Internet at: <http://en.wikipedia.org/wiki/methylisothiazolinone>.
Rieger et al., CTFA Cosmetic Ingredient Handbook, 1st ed., Nikitakis ed., publ. The Cosmetic, Toiletry and Fragrance Association, Inc., pp. 55, 63, 69-70, 75, 77, 78, 80-84, 85-86, 87-97, and 99-100 (1988).
Technical Data Sheet of Hydroxypropyl Guar Gum provided by Hainian Zhongxin Chemical Co., Ltd., Hainan, China (2011).
Wadhwani et al., Effect of various solvents on bacterial growth in context of determinig MIC of various antimicrobials, The Internet J. Microbiol., 7(1):1-6 (2009).

\* cited by examiner

*Primary Examiner* — Yong Chu
*Assistant Examiner* — Sonya Wright
(74) *Attorney, Agent, or Firm* — Marshall, Gerstein & Borun LLP

(57) ABSTRACT

Disclosed herein is an antibacterial cleansing composition. The cleansing composition is free of triclosan and comprises lactic acid/lactate, at least one C2 to C3 alcohol, and glutamate diacetate. Lactic acid/lactate is present in the composition in an amount of about 5 weight percent (wt %) to about 15 wt %, based on the total weight of the composition. The C2 to C3 alcohol is present in an amount of about 1 wt % to about 20 wt %, based on the total weight of the composition. Glutamate diacetate is present in an amount of about 0.05 wt % to about 5 wt %. The pH of the composition is about 4 to about 5. The triclosan-free cleansing composition according to the invention has superior antibacterial activity that surpasses comparable triclosan-free formulations that do not contain glutamate diacetate.

24 Claims, No Drawings

TRICLOSAN-FREE ANTIBACTERIAL SOAP

FIELD OF THE INVENTION

The invention is directed to an antibacterial liquid cleansing composition suitable for use in a personal care product. The antibacterial liquid cleansing composition according to the invention comprises lactic acid/lactate, at least one C2 to C3 alcohol, and glutamate diacetate, and does not contain triclosan. The antibacterial liquid cleansing composition according to the invention demonstrates superior antibacterial activity compared to triclosan-free formulations not containing glutamate diacetate.

BACKGROUND OF THE INVENTION

Antimicrobial liquid cleansing products such as antibacterial soaps and hand sanitizers have risen in popularity over the past decade and are now a billion-dollar industry. Such antibacterial cleansers were once largely confined to medical settings. Virulent outbreaks of bacterial infections including *Escherichia coli* and *Listeria monocytogenes* among the general population in recent years, however, have fueled consumer demand for personal care products that eliminate skin microorganisms. Such consumer demands are reflected in the market place. For example, a recent survey of soap products currently on the market determined that about 75% of liquid soaps contain antibacterial agents.

The antibacterial compound most frequently found in consumer products is 5-chloro-2-(2,4-dichlorophenoxy)phenol, more commonly known as triclosan. Triclosan has been in use for decades and is present in almost half of the liquid soaps currently on the market. Triclosan can also be found in hundreds of other product categories, including toothpaste, clothing, and toys. Triclosan has proven broad-spectrum efficacy against most Gram-positive and Gram-negative bacteria. The compound exerts bactericidal activity through multiple mechanisms, including the inhibition of fatty acid synthesis in bacterial cells. In personal care products, triclosan is generally used in an amount of about 0.1 weight percent (wt %) to about 0.5 wt %, based on the total weight of the composition, in order to provide sufficient antimicrobial activity. For example, a commercially available antibacterial cleansing composition containing 0.5 wt % triclosan and 5.4 wt % lactic acid/lactate in a liquid soap base comprising water, about 4 wt % sodium laureth sulfate, 4 wt % sodium cumenesulfonate, 10 wt % propylene glycol, and 1 wt % cocamidopropyl betaine and having a pH of about 4.5 is known in the art. Other antibacterial cleansing compositions known in the art having pH values between about 4.2 and 4.5 comprise about 0.3 wt % triclosan and 10 wt % lactic acid/lactate as active antimicrobial agents in a similar liquid soap base further including about 4.5 wt % ethyl alcohol.

The safety of triclosan is controversial, however. Some scientists have warned that overuse of the compound could cause resistant strains of bacteria to develop. There is also concern over the effects of triclosan on humans. The chemical has been found to accumulate within the body, and recent studies have linked triclosan to the development of allergies and disruption of hormone regulation. Because of the potential safety issues associated with triclosan, some consumer groups have called for a ban on its use. Indeed, the hazards of triclosan are reflected in its registration as a pesticide with the Environmental Protection Agency. In view of the aforementioned health concerns, both the Food and Drug Administration and Environmental Protection Agency are currently re-evaluating the safety of triclosan in consumer products. However, despite concerns over triclosan's safety, its use remains widespread due to the compound's superior antibacterial properties. With the safety of triclosan in question and an unwaning threat of harmful bacteria, however, there exists a need for antibacterial consumer products that are triclosan-free, but still effective at killing microorganisms, particularly in areas or situations where infection is medically indicated, such as in hospitals, in community medical facilities, in dental institutions, in clinics of schools and of nursing homes, in the workplace, and in the home.

SUMMARY OF THE INVENTION

The invention provides an antibacterial liquid cleansing composition that is free of triclosan and comprises lactic acid/lactate, at least one C2 to C3 alcohol, and glutamate diacetate. Lactic acid/lactate is typically present in the composition in an amount of about 5 wt % to about 15 wt %. The C2 to C3 alcohol (e.g., ethyl alcohol, n-propyl alcohol, isopropyl alcohol, or combinations thereof) is typically present in an amount of about 1 wt % to about 20 wt %. Glutamate diacetate is typically present in an amount of about 0.05 wt % to about 5 wt %. The pH of the composition is generally between about 4 and about 5. The triclosan-free cleansing composition according to the invention has surprisingly superior antibacterial activity against *E. coli*, in particular relative to comparable compositions not containing glutamate diacetate.

The invention also provides a method of sanitizing comprising applying an antibacterial liquid cleansing composition that is free of triclosan and comprises lactic acid/lactate, at least one C2 to C3 alcohol (e.g., ethyl alcohol, n-propyl alcohol, isopropyl alcohol, or combinations thereof), and glutamate diacetate to a surface to eliminate microorganisms.

DETAILED DESCRIPTION OF THE INVENTION

The invention provides a liquid cleansing composition comprising lactic acid/lactate, at least one C2 to C3 alcohol, and glutamate diacetate that is free of triclosan and surprisingly exhibits superior antimicrobial activity, in particular relative to comparable compositions not containing glutamate diacetate.

Surprisingly, the liquid cleansing composition according to the invention comprising lactic acid/lactate, a relatively low concentration of at least one C2 to C3 alcohol, and glutamate diacetate, without any additional conventional antimicrobial agents such as triclosan, exhibits potent bactericidal properties. Advantageously, the liquid cleansing composition fulfills the requirements of the European standard EN1499 for evaluating whether a hygienic hand wash product reduces the release of transient flora when used for washing the artificially contaminated hands of volunteers.

Even more surprisingly, the triclosan-free liquid cleansing composition according to the invention demonstrates antibacterial properties that are superior to comparable triclosan-free formulations not containing glutamate diacetate. For example, the liquid cleansing composition according to the invention comprising lactic acid/lactate, ethyl alcohol, and glutamate diacetate achieved over a 7.5-fold improvement in reduction of *Escherichia coli* compared to a reference product, as assessed by the EN1499 protocol. This improvement is statistically significant as determined by a nonparametric WILCOXON matched-pairs prognostic rank test. Under the same testing conditions, a triclosan-free liquid cleansing composition comprising lactic acid/lactate and ethyl alcohol, but not containing glutamate diacetate, only achieved a 1.5-fold improvement in reduction of *Escherichia coli* compared to the reference product. This improvement was not statistically significant as determined by a nonparametric WILCOXON matched-pairs prognostic rank test.

The liquid cleansing composition according to the invention advantageously provides a safe alternative to products containing controversial antimicrobial agents such as triclosan, without sacrificing antibacterial efficacy. Moreover, the liquid cleansing compositions according to the invention generally are free of additional conventional antimicrobial agents, including but not limited to, amoxicillin, ampicillin, amphotericin, azithromycin, aztreonam, bacitracin, cephalothin, chloramphenicol, clavulanic acid, clindamycin, ciprofloxacin, doxycycline, erythromycin, gantrisin, gentamicin, imipenem, isoniazid, methicillin, nalidixic acid, nystatin, para-aminosalicylic acid, penicillin, polymyxin, rifamycin, streptomycin, sulfanilamide, tetracycline, trimethoprim, and vancomycin. Further conventional antimicrobial agents commonly used for cleansing compositions include, but are not limited to, triclocarban, trichlorocarbamide, chloroxylenol, chlorhexidine, chlorhexidine gluconate, iodine, and hexachlorophene, and the liquid cleansing compositions according to the invention generally are free of the foregoing as well.

Lactic acid and its counter anion lactate can be derived from various sources including milk and sugar beets. Lactic acid is most commonly used in personal care products as an exfoliant, not for any antibacterial properties. It is well known that lactic acid exists in equilibrium with its counter anion lactate and that the relative concentrations of these two species depends on the pH of the system. Hence, the amount of lactic acid initially added to a composition will not directly correspond to the amount of lactic acid present in the composition after equilibrium is achieved, particularly when the pH of the composition differs from the pH of 100% lactic acid. Lactic acid/lactate is generally present in the liquid cleansing compositions according to the invention in an amount of about 5 wt % to about 15 wt %, about 7 wt % to about 13 wt %, about 9 wt % to about 12 wt %, and/or about 10 wt % to about 11 wt %, for example, about 10 wt %, based on the total weight of the composition.

C2 to C3 alcohols are known bactericides, however, a high concentration of alcohol is typically needed to confer antimicrobial properties to a product formulation. For example, ethyl alcohol in a hand sanitizer gel is typically present in an amount of at least 50 wt %, most frequently between about 60 wt % and about 90 wt %, to provide sufficient antimicrobial activity and thus function as an active antimicrobial ingredient. In contrast, at least one C2 to C3 alcohol is generally present in the invention an amount of about 1 wt % to about 20 wt %, about 2 wt % to about 15 wt %, about 3 wt % to about 10 wt %, and/or about 4 wt % to about 6 wt %, for example, about 5 wt %.

Glutamate diacetate is commonly supplied as the tetrasodium salt, tetrasodium glutamate diacetate. Other suitable counterions include, but are not limited to, potassium and ammonium. Without wishing to be bound by theory, glutamate diacetate is believed to substantially improve the performance of liquid cleansing compositions by chelating metal ions that would otherwise interfere with the performance of the liquid cleansing compositions. For example, metals including, but not limited to, $Ca^{2+}$ and $Mg^{2+}$ can interfere with the performance of a liquid cleansing composition by forming hard water metal salt precipitates (i.e., soap scum) and metals including, but not limited to, copper, manganese, and iron can interfere with the performance of a liquid cleansing composition by catalyzing decomposition of components of the liquid cleansing composition. Further, without wishing to be bound by theory, glutamate diacetate is believed to substantially improve the performance of liquid cleansing compositions by chelating metal ions (e.g., calcium ions and magnesium ions) present in the membrane of bacterial cells and other microorganisms, thereby increasing the permeability of the membrane to biocides. In addition, the specific selection of glutamate diacetate as a chelating agent has been found to surprisingly confer enhanced antimicrobial activity even relative to cleansing compositions containing other chelating agents. In formulations containing one or more preservatives, glutamate diacetate has been found to surprisingly boost the effectiveness of a variety of preservatives, thereby reducing the amount preservative needed to achieve the desired effect. Glutamate diacetate is generally present in the liquid cleansing compositions according to the invention in an amount of about 0.05 wt % to about 5 wt %, about 0.1 wt % to about 3 wt %, about 0.1 wt % to about 1 wt %, and/or about 0.1 wt % to about 0.3 wt %, for example, about 0.2 wt %.

The pH of the liquid cleansing composition according to the invention is generally between about 4 to about 5, for example, about 4.0 to about 4.9, about 4.1 to about 4.8, about 4.2 to about 4.8, about 4.2 to about 4.7, about 4.2 to about 4.6, about 4.2 to about 4.5, and/or about 4.2 to about 4.4, for example, about 4.15 to about 4.25. While the pH range can vary between about 4 to about 5 as described above, cleansing compositions having a pH of about 4.2 to about 4.3 have been found to surprisingly demonstrate enhanced antimicrobial activity relative to comparable cleansing compositions having higher pH values. Further, cleansing compositions having a pH of about 4.2 to about 4.3 advantageously avoid undesirable skin irritation compared to cleansing compositions having lower pH values.

The cleansing composition according to the invention typically further contains additional components including, but not limited to, solvents, surfactants, hydrotropes, and pH adjusting agents. In some embodiments, the invention may also further include additional components such as preservatives, viscosity enhancers, and skin conditioning agents.

In the liquid cleansing composition according to the invention, the lactic acid/lactate and C2 to C3 alcohol are typically dissolved in a solvent. The total amount of solvent in the liquid cleansing composition according to the invention is typically between about 10 wt % and about 85 wt % and/or between about 60 wt % and about 80 wt %, for example, about 70 wt %. The solvent may be comprised of, for example, a combination of water and a hydric solvent which is different from the C2 to C3 alcohol. Examples of suitable hydric solvents include, but are not limited to, hydroxyl-containing compounds such as methanol, ethylene glycol, propylene glycol, glycerol, diethylene glycol, dipropylene glycol, tripropylene glycol, hexylene glycol, butylene glycol, and sorbitol. Additional solvents that are contemplated for use with the present invention and may be substituted for those disclosed herein are described in the *CTFA Cosmetic Ingredient Handbook, First Edition*, Cosmetic, Toiletry, and Fragrance Association, Washington D.C., (1988) at pages 85-86, (the CTFA Handbook"), which are hereby incorporated herein by reference.

One or more surfactants is generally present in the liquid cleansing composition according to the invention. The surfactant(s) can be added to the liquid cleansing composition according to the invention to improve cleansing power and foam production. The total amount of surfactant in the liquid cleansing composition according to the invention is typically between about 1 wt % and about 20 wt % and/or about 2 wt % and about 10 wt %, for example, about 5 wt %. Non-limiting examples of suitable surfactants include but are not limited to sodium laureth sulfate and ammonium lauryl sulfate. Foaming agent surfactants such as cocamidopropyl betaine and shea butteramidopropyl betaine may also be used in the invention. Examples of commercially available foaming agent surfactants include Tego® Betain F 50 (Evonik Industries) and Jeeteric CAB-LC (Jeen International Corporation). Another type of surfactant that may be included in the composition is a hydrotrope. A hydrotrope enhances the water solubility of the other components in the formulation. Representative hydrotropes include, but are not limited to, alkyl aryl sulfonate compounds including sodium cumenesulfonate, ammonium cumene sulfonate, ammonium xylene sulfonate, potassium tolulene sulfonate, and xylene sulfonic acid. The total amount of hydrotrope in the liquid cleansing composition according to the invention is typically between about 1 wt % and about 20 wt % and/or about 2 wt % and about 10 wt %, for example, about 4 wt %. Additional surfactants suitable for use with the invention are disclosed in the CTFA Handbook at pages 87-97, which are hereby incorporated herein by reference.

In one embodiment, the liquid cleansing composition further comprises a pH adjusting agent. The pH adjusting agent may be added in an amount to achieve a pH within the range of about 4 to about 5, about 4.0 to about 4.9, about 4.1 to about 4.8, about 4.2 to about 4.8, about 4.2 to about 4.7, about 4.2 to about 4.6, about 4.2 to about 4.5, and/or about 4.2 to about 4.4, for example, about 4.2 to about 4.3, for the liquid cleansing composition according to the invention. The pH adjusting agent may be added to partially neutralize lactic acid (i.e., convert the lactic acid to its counter anion lactate) present in the liquid cleansing composition. The pKa of lactic acid is 3.79, so since a liquid cleansing composition according to the invention has a pH higher than the pKa of lactic acid, more lactate is present than lactic acid. The higher concentration of lactate relative to lactic acid generally minimizes skin irritation while still presenting excellent antimicrobial activity, but the relative amount of lactic acid to lactate in the cleansing composition is also considered to be significant given the findings described above with respect to the pH values of the cleansing compositions. The proximity of the slightly acidic pH of the invention to the normal pH of skin also serves to reduce damage to the epidermis. Suitable pH adjusting agents include, but are not limited to, strong bases such as sodium hydroxide and potassium hydroxide. Buffering agents such as sodium acetate, sodium citrate, and sodium lactate may also serve as pH adjusting agents in the invention, again provided that the resulting pH of the liquid cleansing composition according to the invention is within the described range. More examples of pH adjusting agents suitable for use in the liquid cleansing composition according to the invention are described in the CTFA handbook at page 77, which is hereby incorporated herein by reference.

Optionally, preservatives may be present in the invention. The total concentration of preservatives in the composition is less than about 3 wt %, for example, less than about 2 wt %. Examples of suitable preservatives include phenoxyethanol, sodium benzoate, benzyl alcohol, methylchloroisothiazolinone and methylisothiaziolinone. Examples of commercially available preservatives include Euxyl® K100 (Schulke Inc.) and Kathon™ CG (Dow Chemical Company). One skilled in the art would understand that other preservatives, including but not limited to those based on organic acids such as potassium sorbate may also be used in the liquid cleansing composition according to the invention. Others examples of preservatives contemplated for use in the liquid cleansing composition according to the invention are disclosed in the CTFA handbook at page 78, which is hereby incorporated herein by reference.

Additives are frequently included in cleansing formulations to improve the aesthetic properties of a product. For example, a viscosity enhancing agent may be added to the invention to provide the antibacterial composition with a desired texture and feel. A viscosity enhancing agent may be present in an amount less than about 1 wt %, for example, about 0.9 wt %. Suitable viscosity enhancing agents include, for example, hydroxypropyl guar, seaweed extracts, synthetically modified versions of cellulose and/or starch, propylene glycol alginate, carboxymethyl locust bean gum, carboxymethyl guar, xanthan gum, carboxymethylcellulose, hydroxyethylcellulose, sodium alginate and other salts of alginic acid, carrageenan, gum arabic, gum karaya, gum tragacanth, gum ghatti, guar gum, locust bean gum, and other polysaccharides. Other examples of viscosity enhancing agents contemplated for use in the liquid cleansing composition according to the invention are disclosed in the CTFA handbook at pages 99-100, which are hereby incorporated herein by reference.

Skin conditioning agents are optionally present in the formulation. Skin conditioning agents improve cosmetic benefits and appeal to consumers. A non-limiting example of a suitable skin conditioning agent is a vitamin derivative such as disodium lauriminodipropionate tocopheryl phosphates. Additional examples of skin conditioning agents contemplated for use in the liquid cleansing composition according to the invention are described in the CTFA handbook at pages 80-84, which are hereby incorporated herein by reference.

Other ingredients known in the art to improve the commercial appeal of the product may be present in the invention. Examples include humectants, fragrances, dyes, and antioxidants, all of which are well-known and disclosed in the CTFA handbook at pages 55, 63, 69-70, and 75, which are hereby incorporated herein by reference.

A liquid cleansing composition according to the invention may be applied to a palm of a hand to eliminate microorganisms. A cleansing composition according to the invention may be applied in a similar fashion to additional areas of the body or other surfaces to reduce bacterial contamination.

In one embodiment, a liquid cleansing composition according to the invention is prepared by combining water, about 10 wt % lactic acid, about 5 wt % ethyl alcohol, about 0.2 wt % tetrasodium glutamate diacetate, about 2 wt % sodium hydroxide (added as a 33% solution), and, optionally, propylene glycol, sodium cumenesulfonate, sodium laureth sulfate, cocamidopropyl betaine, and phenoxyethanol and sodium benzoate as preservatives.

In the following Examples, triclosan-free liquid cleansing compositions according to the invention were tested for antibacterial properties according to the European standard EN1499 for evaluating whether a hygienic hand wash product reduces the release of transient flora when used for washing the artificially contaminated hands of volunteers. The formulations according to the invention were compared to triclosan-free liquid soaps not containing glutamate diacetate. Surprisingly, the invention fulfilled the stringent requirements of the EN1499 standard. Examples 1 and 2 demonstrate the bactericidal efficacy of the liquid cleansing invention comprising lactic acid/lactate, at least one C2 to C3 alcohol, and glutamate diacetate compared to similar triclosan-free compositions not containing glutamate diacetate.

EXAMPLES

Example 1

Composition A, a triclosan-free cleansing composition according to the invention, was evaluated for antibacterial properties using a quantitative practical test performed according to the European standard EN1499 for evaluating whether a hygienic hand wash product reduces the release of transient flora when used for washing the artificially contaminated hands of volunteers. The composition of the triclosan-free cleansing composition according to the invention follows:

| Ingredient | Trade Name (Supplier) | Weight % of Ingredient |
|---|---|---|
| Water | Demineralized Tap Water (NWL Netherlands Production BV) | 47.46 |
| Lactic Acid (90%) | PURAC ® HiPure 90 (Brenntag) | 11.10 |
| Propylene Glycol | 1,2-Propylene Glycol USP (HELM Chemicals) | 10.00 |
| Sodium Cumenesulfonate (40%) | Na-Cumolsulfonat 40 (Brenntag) | 10.00 |
| Sodium Hydroxide (33%) | Sodium Hydroxide 33% (Brenntag) | 6.30 |
| Sodium Laureth Sulfate (70%) | Tensagex E0C670 (TensaChem) | 5.60 |
| Alcohol Denat. (96% ethanol + 5% isopropanol) | Ethanol SURFIN 96% + 5% Isopropylalcohol (HELM Chemicals) | 5.00 |
| Cocamidopropyl Betaine (38%) | TEGO ® Betain F 50 (Evonik Industries) | 2.6500 |
| Phenoxyethanol (99%) | SM Phenoxyethanol (Schülke) | 0.9925 |
| Sodium Benzoate | Sodium Benzoate BP2000 (Azelis) | 0.5000 |
| Tetrasodium Glutamate Diacetate (47.4%)/Sodium Hydroxide (1.9%) | Dissolvine ® GL-47-S (Caldic) | 0.4000 |

Composition A has a pH of about 4.2 to about 4.3.

The ability of Composition A to reduce bacterial populations of *Escherichia coli* was tested. The reduction from the initial population was calculated following exposure to the product for 1 minute. The same protocol was also used to evaluate a reference product (Kalisoap), an ethanol-containing soap containing 50 parts by weight linseed oil, 9.5 parts by weight potassium hydroxide, 7 parts by weight ethanol, and distilled water as needed to bring the soap to a total of 100 parts by weight. The ratio of the number of test organisms released from the fingertips of artificially contaminated hands before and after the hygienic hand wash (the "reduction factor") was determined. To compensate for extraneous influences, the reduction factor of Composition A was compared to the reduction factor of the reference product, which was obtained with the same subjects, on the same day and under comparable environmental conditions. The results of the studies are summarized below.

| Microorganism | Exposure Time | COMPOSITION A | REFERENCE |
|---|---|---|---|
| | | Mean $Log_{10}$ Reduction (n = 15) | |
| *Escherichia coli* K 12 (NCTC 10538) | 1 minute | 3.98 | 3.10 |

Composition A in accordance with the invention, surprisingly and unexpectedly exhibited more potent antibacterial properties than the reference product, and fulfilled the requirements of EN 1499 for a hygienic hand wash. This difference in bactericidal efficacy was statistically significant, as determined by the nonparametric WILCOXON matched-pairs prognostic rank test.

As a result of satisfying the EN 1499 requirements, Composition A, a liquid cleansing compositions according to the invention, is suitable for eliminating skin microorganisms in areas or situations where infection is medically indicated, such as in hospitals, in community medical facilities, in dental institutions, in clinics of schools and of nursing homes, in the workplace, and in the home.

Comparative Example 1

Composition B, a triclosan-free cleansing composition not according to the invention but otherwise comparable to Composition A (particularly with respect to lactic acid and ethanol contents), was evaluated for antibacterial properties using a quantitative practical test performed according to the European standard EN1499 for evaluating whether a hygienic hand wash product reduces the release of transient flora when used for washing the artificially contaminated hands of volunteers. The composition of the comparative triclosan-free cleansing composition not according to the invention follows:

| Ingredient | Trade Name (Supplier) | Weight % of Ingredient |
|---|---|---|
| Water | Deionized Water | 48.07 |
| Lactic Acid (90%) | PURAC ® HiPure 90 (PURAC) | 11.10 |
| Propylene Glycol | Propylene Glycol USP (Jeen Int.) | 10.00 |
| Ethyl Alcohol 96% Denatured with Isopropyl Alcohol | SDA 3C | 5.00 |
| Sodium Cumenesulfonate (40%) | Stepanate SCS 40% (Stepan) | 10.0 |
| Sodium Laureth Sulfate (70%) | Steol CS-270 70% (Stepan) | 5.60 |
| Sodium Hydroxide (33%) | Sodium Hydroxide 33% | 6.50 |
| Cocamidopropyl Betaine (40%), Glycerin | Jeeteric CAB-CL (Jeen Int.) | 2.63 |
| Hydroxypropyl Guar | Guar 105 (Gova) | 0.90 |
| Benzyl Alcohol, Methylchloroisothiazolinone, Methylisothiazolinone (21%) | Kathon CG (Dow) | 0.09 |
| Disodium Lauriminodipropionate Phosphates (40%) | Vital ET ® (ISP) | 0.01 |
| Shea Butteramidopropyl Betaine (36%) | Lipex ® Shea Betaine (AarhusKarlshamn) | 0.10 |

Composition B has a pH of about 4.18.

The ability of Composition B to reduce bacterial populations of *Escherichia coli* was tested. The reduction from the initial population was calculated following exposure to the product for 1 minute. The same protocol was also used to evaluate a reference product (Kalisoap), an ethanol-containing soap containing 50 parts by weight linseed oil, 9.5 parts by weight potassium hydroxide, 7 parts by weight ethanol, and distilled water as needed to bring the soap to a total of 100 parts by weight. The results of the studies are summarized below.

| Microorganism | Exposure Time | COMPOSITION B | REFERENCE |
|---|---|---|---|
| | | Mean $Log_{10}$ Reduction (n = 15) | |
| *Escherichia coli* K 12 (NCTC 10538) | 1 minute | 2.98 | 2.79 |

Composition B, not in accordance with the invention, exhibited more potent antibacterial properties than the reference product. This difference in bactericidal efficacy was not statistically significant, as determined by the nonparametric WILCOXON matched-pairs prognostic rank test, and did not fulfill the requirements of EN 1499 for a hygienic hand wash.

The Examples establish that the combination of lactic acid/lactate, at least one C2 to C3 alcohol, and glutamate diacetate in cleansing compositions according to the invention is surprisingly responsible for fulfilling the stringent requirements of EN 1499 for a hygienic hand wash and surpasses the antibacterial efficacy of a comparable composition not containing glutamate diacetate. Lactic acid/lactate, C2 to C3 alcohols, and glutamate diacetate are compounds which are known to be safe, however, and thus the potent bactericidal effects of a composition comprising about 5 wt % to about 15 wt % lactic acid/lactate, about 1 wt % to about 20 wt % C2 to C3 alcohol, and about 0.05 wt % to about 5 wt % glutamate diacetate, with a pH of about 4 to about 5, were completely unexpected. As a result, the liquid cleansing compositions according to the invention offer the benefit of eliminating skin microorganisms in areas or situations where infection is medically indicated, such as in hospitals, in community medical facilities, in dental institutions, in clinics of schools and of nursing homes, in the workplace, and in the home.

The foregoing Examples are provided to further illustrate the invention without being limiting. While particular embodiments of the present invention have been illustrated and described, it would be obvious to those skilled in the art that various other changes and modifications can be made without departing from the spirit and scope of the invention. It is therefore intended to cover in the claims all such changes and modifications that are within the scope of this invention.

What is claimed is:

1. An antibacterial cleansing composition comprising:
   about 5 weight percent (wt %) to about 15 wt % lactic acid/lactate;
   about 1 wt % to about 20 wt % C2 to C3 alcohol; and
   about 0.05 wt % to about 5 wt % glutamate diacetate;
   wherein the composition is free of triclosan, the pH of the composition is about 4 to about 5, and the composition has bactericidal activity against *E. coli*.

2. The composition of claim 1, wherein the lactic acid/lactate is present in an amount of about 7 wt % to about 13 wt %.

3. The composition of claim 2, wherein the lactic acid/lactate is present in an amount of about 10 wt %.

4. The composition of claim 1, wherein the C2 to C3 alcohol is present in an amount of about 2 wt % to about 15 wt %.

5. The composition of claim 4, wherein the C2 to C3 alcohol is present in an amount of about 5 wt %.

6. The composition of claim 1, wherein the C2 to C3 alcohol is ethyl alcohol.

7. The composition of claim 1, wherein the glutamate diacetate is present in an amount of about 0.1 wt % to about 3 wt %.

8. The composition of claim 7, wherein the glutamate diacetate is present in an amount of about 0.2 wt %.

9. The composition of claim 1, wherein the pH of the composition is about 4.0 to about 4.9.

10. The composition of claim 9, wherein the pH of the composition is about 4.2 to about 4.3.

11. The composition of claim 1, further comprising a solvent in an amount of about 10 wt % to about 85 wt %.

12. The composition of claim 11, wherein the solvent is in an amount of about 70 wt %.

13. The composition of claim 11, wherein the solvent is selected from the group consisting of water, propylene glycol, and combinations thereof.

14. The composition of claim 1, further comprising a hydrotrope in an amount of about 1 wt % to about 20 wt %.

15. The composition of claim 14, wherein the hydrotrope is present in an amount of about 4 wt %.

16. The composition of claim 1, further comprising a surfactant in an amount of about 1 wt % to about 20 wt %.

17. The composition of claim 16, wherein the surfactant is present in an amount of about 5 wt %.

18. The composition of claim 16, wherein the surfactant is selected from the group consisting of sodium laureth sulfate, cocamidopropyl betaine, and combinations thereof.

19. The composition of claim 1, further comprising a pH adjusting agent in an amount effective to achieve a composition pH within the range of about 4 to about 5.

20. The composition of claim 19, wherein the pH adjusting agent is present in an amount effective to achieve a composition pH of about 4.2 to about 4.3.

21. The composition of claim 19, wherein the pH adjusting agent is sodium hydroxide.

22. The composition of claim 1, further comprising a preservative in an amount less than about 3 wt %.

23. The composition of claim 22, wherein the preservative is selected from the group consisting of phenoxyethanol, sodium benzoate, and combinations thereof.

24. A method of sanitizing hands comprising applying a composition of claim 1 to a palm of a hand to eliminate skin microorganisms.

* * * * *